US011572322B2

(12) United States Patent
Nesterenko et al.

(10) Patent No.: US 11,572,322 B2
(45) Date of Patent: *Feb. 7, 2023

(54) ALKYL HALIDES CONVERSION INTO ACYCLIC C3-C6 OLEFINS

(71) Applicants: TOTALENERGIES ONETECH, Courbevoie (FR); SULZER MANAGEMENT AG, Winterthur (CH)

(72) Inventors: Nikolai Nesterenko, Nivelles (BE); Gleb Veryasov, Nivelles (BE); Raoul Dethier, Schaerbeek (BE)

(73) Assignees: TOTALENERGIES ONETECH, Courbevoie (FR); SULZER MANAGEMENT AG, Winterthur (CH)

(*) Notice: Subject to any disclaimer, the term of this patent is extended or adjusted under 35 U.S.C. 154(b) by 0 days.

This patent is subject to a terminal disclaimer.

(21) Appl. No.: 17/777,829

(22) PCT Filed: Nov. 20, 2020

(86) PCT No.: PCT/EP2020/082827
§ 371 (c)(1),
(2) Date: May 18, 2022

(87) PCT Pub. No.: WO2021/099539
PCT Pub. Date: May 27, 2021

(65) Prior Publication Data
US 2022/0356127 A1 Nov. 10, 2022

(30) Foreign Application Priority Data

Nov. 22, 2019 (EP) .................... 19315139

(51) Int. Cl.
*C07C 1/26* (2006.01)
*B01J 35/00* (2006.01)
*B01J 29/40* (2006.01)
*B01J 37/28* (2006.01)
*B01J 37/00* (2006.01)
*B01J 37/10* (2006.01)
*B01J 37/02* (2006.01)

(52) U.S. Cl.
CPC ............... *C07C 1/26* (2013.01); *B01J 29/40* (2013.01); *B01J 35/006* (2013.01); *B01J 37/0009* (2013.01); *B01J 37/0201* (2013.01); *B01J 37/10* (2013.01); *B01J 37/28* (2013.01); *B01J 2229/16* (2013.01); *B01J 2229/37* (2013.01); *B01J 2229/42* (2013.01); *C07C 2529/40* (2013.01)

(58) Field of Classification Search
CPC ........ B01J 37/28; B01J 37/10; B01J 37/0009; B01J 37/0201; B01J 35/006; B01J 29/40; B01J 2229/16; B01J 2229/42; B01J 2229/37; C07C 1/26; C07C 2529/40
USPC .................................. 585/641, 642
See application file for complete search history.

(56) References Cited

U.S. PATENT DOCUMENTS

| 2008/0188701 | A1 | 8/2008 | Qi et al. |
| 2016/0200642 | A1 | 7/2016 | Ghosh et al. |
| 2016/0347681 | A1 | 12/2016 | Ghosh et al. |
| 2016/0347682 | A1 | 12/2016 | Ghosh |
| 2017/0057886 | A1 | 3/2017 | Fickel |

FOREIGN PATENT DOCUMENTS

| CN | 106140259 A | 11/2016 |
| EP | 0162590 A1 | 11/1985 |
| WO | 2016007322 A1 | 1/2016 |
| WO | 2016099775 A1 | 6/2016 |

OTHER PUBLICATIONS

Machine Translation of the claims for CN 106140259 A Nov. 23, 2016.*
Machine Translation of the description for CN 106140259 A, Nov. 23, 2016.*
Monica Gamero et al, "Role of Shape Selectivity and Catalyst Acidity in the Transformation of Chloromethane into Light Olefins", Industrial & Engineering Chemistry Research, (Aug. 7, 2015), vol. 54, No. 32, pp. 7822-7832.
International Search Report and Written Opinion issued in Application No. PCT/EP2020/082827 dated Jan. 21, 2021; 10 pages.

* cited by examiner

*Primary Examiner* — Elizabeth D Wood
(74) *Attorney, Agent, or Firm* — Ewing & Jones, PLLC

(57) ABSTRACT

The present disclosure relates to a process for converting one or more alkyl halides to acyclic C3-C6 olefins, said process comprising the steps of (a) providing a feedstream comprising one or more alkyl halides; (b) providing a catalyst composition; and (c) contacting said feedstream with said catalyst composition under reaction conditions. The process is remarkable in that said process further comprises a step of steaming said catalyst composition before the step (c) and in that said catalyst composition comprises one or more zeolites and a binder, wherein said one or more zeolites comprise at least one 10-membered ring channel. The present disclosure further relates to the use of a catalyst composition in said process, said catalyst composition comprising one or more zeolites and a binder, wherein said catalyst composition is steamed before use.

20 Claims, 2 Drawing Sheets

ALKYL HALIDES CONVERSION INTO ACYCLIC C3-C6 OLEFINS

CROSS-REFERENCE TO RELATED APPLICATIONS

This application claims the benefit of PCT/EP2020/082827 filed Nov. 20, 2020, which claims priority from EP 19315139.6 filed Nov. 22, 2019, which are incorporated herein by reference in their entireties for all purposes.

FIELD OF THE DISCLOSURE

The present disclosure relates to a process for converting one or more alkyl halides selectively into acyclic C3-C6 olefins.

BACKGROUND OF THE DISCLOSURE

Olefins are used to make numerous downstream products. Starting from an alkane, and methane, in particular, it is feasible to obtain the corresponding alkyl halide, for example, methyl halide. Alkyl halides can be then transformed into olefins. By adjusting the reaction conditions and employing a specific catalyst, the ratios of these various olefins may be modified, leading to the obtaining of the desired effluents, that can be then separated by known technology. The process for converting one or more alkyl halides into olefins, namely the second step of the two-step process for producing olefins from alkanes, has already been thoroughly studied.

In US 2016/0347682, a crystalline zeolite catalyst having an STI framework topology, such as SSZ-75, was used. The document does not contain any examples of catalyst performance. It is assumed that the transformation of the alkyl halide on this catalyst in the temperature range between 300° C. and 500° C., and under the pressure range 1-2.4 bars, occurs with selectivity to ethylene equal to or less than 10%, with selectivity to propylene higher than 50% and with selectivity in olefin product being C5 and/or C5+ olefins less than 10%. No data on conversion and stability of the catalyst is given. This catalyst does not seem to be suitable to produce higher olefins.

In US 2017/0057886, an aluminosilicate zeolite catalyst, i.e. a chabazite zeolite of the SSZ-13 type, described as having a higher acidity than a silicoaluminophosphate catalyst (due to the presence of aluminium ions in the crystal structure instead of silicon atoms), has been used in the olefin production from methyl chloride. The experiment was conducted at a temperature of 450° C., WHSV of 2.7 h$^{-1}$, and pressure of 0 MPa in order to obtain selectivity in ethylene of 34.95% and in propylene of 33.99% at substantially complete conversion. The catalyst stability was about 1 hour-on-stream (very fast deactivation). Selectivity in the fraction C4+ is not reported. The inventors assume also a potential co-feeding with MeOH. Based on the description, the material is only suitable for the fluidized bed reactors due to a very short period of stability and results mainly in ethylene production.

In WO 2016/099775, the methyl chloride transformation into olefins was studied with a SAPO zeolite catalyst. After 20 h on stream, a conversion of 90.7% was achieved and a good selectivity in ethylene (40.4%) and propylene (42.9%) was observed. However, the selectivity to C4 olefins decreases to 11.1%.

US 2008/0188701 describes the use of a silicoaluminophosphate molecular sieve catalyst, which comprises 50 wt. % of SAPO-34 molecular sieve as active component and 50 wt. % of alumina as a matrix. At relatively low temperature (350° C.), 28.46% of methyl chloride was converted affording a selectivity in ethylene of 28.31%, in propylene of 42.08% and in C4 olefins of 17.42%. At higher temperatures, the formation of ethylene is favoured. Using SAPO-11 molecular sieve at 450° C. instead of SAPO-34 (subsequently still with alumina as a binder) has however allowed for a reduction in ethylene selectivity up to 5.96%, which is still a relatively elevated level. Besides the conversion reaches only 62.8%.

In US 2016/0200642, 10-membered ring-containing ZMS-5 zeolite, presenting a silica-to-alumina ratio (SAR) comprised between 30 and 1192, is subjected to a contact with a methyl chloride under reaction conditions sufficient to produce an olefin hydrocarbon product comprising C2 to C4 olefins, wherein the selectivity of the C2 to C4 olefins is at least 85% at 20% alkyl halide conversion. The methyl chloride conversion to olefins was carried out at 350° C.

At high SAR (1192), a poor selectivity in ethylene (6.5%) while a high selectivity in C3-05+(89.3%) has been obtained. No trace of aromatics has been detected. A weak conversion (8.6%) after 20 h time on stream has been measured.

At lower SAR (334), the lowest selectivity in C2 (2.6%) has been attained while it was compensated by a slightly higher selectivity in C3-C5+(91.6%). Traces of aromatics (0.2%) were detected. However, the conversion in methyl chloride that has been reached at those conditions was of 45.1% after 20 h time on stream.

The catalyst thus suffers from deactivation, which does not allow to use it in a fixed bed reactor for C3-C6 olefins production. When catalyst with SAR as low as 30 is used, the conversion increases up to 96.6% after 20 h time on stream, but the selectivity to ethylene is of 3.0% and a high number (>17%) of aromatic compounds are generated.

In US 2016/0347681, the deactivation of the catalyst during methyl chloride conversion is addressed. The same zeolite, as in US 2016/0200642, having a silica-to-alumina ratio (SAR) of 278, and being ion-exchanged, for example with magnesium, has been demonstrated as presenting a high selectivity in C3 (51.2%) and C4 (16.8%) olefins compared to a poor selectivity in ethylene formation (6.2%). The conversion in methyl chloride has been improved to 77.6% after 3 h time on stream under those reaction conditions (still carried out at 350° C.).

However, one should mention that this solution cannot be used industrially. At a certain moment, the catalyst still needs to be regenerated. So, the zeolite-containing Mg or Ca chlorides (5-10% wt. % of Cl) and carbon depositions will be subjected in contact with air. The reaction will result in the formation of individual halogens, HCl, CO$_x$ and water. The presence of Cl$_2$ and HCl together with water at very high temperature (550-600° C.) will result in an irreversible deactivation of zeolite via dealumination. So, the amount of metals on zeolites needs to be limited.

One should mention that the literature describes the applications of MFI zeolites structure for the conversion of CH$_3$Cl. The interest in that reaction is linked to the Cl-mediated conversion of CH$_4$ to light olefins with the recycling of Cl$_2$ back to the reaction medium:

$$CH_4 + Cl_2 \rightarrow CH_3Cl + CH_2Cl_2 + CHCl_3 + HCl \quad (1)$$

$$CH_3Cl \rightarrow olefins + HCl \quad (2)$$

$$HCl + O_2 \rightarrow H_2O + Cl_2 \quad (3)$$

In other words, methane is first transformed to methyl chloride derivatives (1), with the following conversion of methyl chloride to light olefins (2) and recovering of the $Cl_2$ from HCl via oxidation (3) to recycle back to the step (1).

However, the conversion of $CH_4$ to Cl-derivatives is not very selective to mono-chloride (see step 1). A very significant amount of di-, and tri-chlorides are formed already at a low conversion level of $CH_4$.

$CH_3Cl$ could be selectively converted to light olefins but the catalyst stability still hampers any further development and requires a very sophisticated and expensive reactor design, which needs to be manufactured with noble metallurgy.

In addition, the conversion of HCl to $Cl_2$ is highly energy-intensive.

All the above mentioned makes the process of the Cl-mediated conversion of $CH_4$ to olefins economically unfeasible, very complex industrially, and still requires a better catalyst solution for $CH_3Cl$ conversion.

The description of the prior art shows that there is a lack of catalyst composition that can efficiently direct the conversion of alkyl halides into higher olefins with a low level of ethylene formation. Either the catalysts are not structurally adapted to the formation of higher olefins, or they are described as producing those higher olefins but with still an amount of ethylene and possibly other by-products that can be undesirable.

EP 0162590 discloses a process for converting monohalomethane to aliphatic hydrocarbons in which the catalyst is a gallosilicate having an MFI structure and loaded with at least one modifying cation selected from hydrogen and metals of groups I to VIII of the periodic table and is steamed before use.

CN 106 140 259 discloses a process to transform methyl bromide to isobutylene (i.e. an acyclic C4 olefin) by contacting methyl bromide and a catalyst which comprises a ZSM-5 molecular sieve carrier. The ZSM-5 molecular sieve carrier is treated with water vapour and is combined with zinc oxide or another oxide (from titanium, zirconium, cerium or lanthanum) before the reaction.

However, such processes generate by-products, such as halides, that are corrosive and difficult to remove from the product stream.

In other words, the direct conversion of one or more alkyl halides to non-cyclic/acyclic C3-C6 olefins, with a limited amount of ethylene, and, in particular, on the substantially metal-free catalyst with stable performance has not yet been described.

The present disclosure has for objective to provide a process wherein the conversion of one or more alkyl halides into olefins lead selectively to the formation of acyclic C3-C6 olefins. In particular, the present disclosure has for objective to provide a process wherein the production of olefins from one or more alkyl halides has an improved selectivity toward acyclic C3-C6 olefins; preferably with reduced selectivity to ethylene (i.e. less than 2% of selectivity to ethylene) and with reduced selectivity to aromatics (i.e. less than 5% of selectivity to aromatics). The present disclosure has also for objective to provide a process wherein the production of olefins from one or more alkyl halides has an improved selectivity toward acyclic C3-C6 olefins and at the same time a high conversion rate (>60% per pass).

SUMMARY OF THE DISCLOSURE

According to a first aspect, the disclosure provides a process for converting one or more alkyl halides to acyclic C3-C6 olefins, preferentially a process for converting one or more alkyl halides to acyclic C3-C6 mono-olefins, said process comprising the following steps:
a) providing a feedstream comprising one or more alkyl halides; optionally, diluted in at least one diluent;
b) providing a catalyst composition; and
c) contacting said feedstream with said catalyst composition under reaction conditions the process is remarkable in that it further comprises a step of steaming said catalyst composition before the step (c) and in that said catalyst composition comprises one or more zeolites and a binder, wherein said one or more zeolites comprise at least one 10-membered ring channel and contain less than 5000 wt. ppm of transition metals as determined by XRF based on the total weight of the one or more zeolites; and further wherein said one or more zeolites of the catalyst composition have a Si/Al molar ratio in the framework of the zeolite of at least 10 as determined by TPD before the step of steaming.

Surprisingly, it has been found that both a high selectivity to acyclic C3-C6 olefins and high conversion, and subsequently a high yield, can be achieved with the use of a catalyst composition wherein at least one zeolite has a structure shaped with a binder. The presence of the binder, preferentially a silica binder, allows for enhancing the selectivity toward acyclic C3-C6 olefins while keeping at the same time the selectivity to ethylene and aromatics low. Indeed, as demonstrated in the examples, a selectivity of at least 70% for the acyclic C3-C6 olefins can be achieved together with a conversion rate of the one or more alkyl halides of at least 20%. In addition, as demonstrated in the examples, a selectivity of at least 75% for the acyclic C3-C6 olefins can be achieved together with selectivity to ethylene of less than 5%, preferably less than 1% and with selectivity to aromatics of less than 15%, preferably less than 11%.

In a preferred embodiment, one or more zeolites of the catalyst composition are free of metal other than aluminium.

For example, said one or more zeolites of the catalyst composition are free of gallium and/or cerium and/or zinc. In a more general way, the one or more zeolites of the catalyst composition are free of transition metals, and/or are free of rare earth elements, and/or are free of lanthanides, and/or are free of alkaline earth metals, and/or are free of alkali metals.

In a preferred embodiment, said one or more zeolites contain less than 1000 wt. ppm of alkali metals as determined by XRF based on the total weight of the one or more zeolites and/or less than 2500 wt. ppm of transition metals as determined by XRF based on the total weight of the one or more zeolites.

For example, said one or more zeolites of the catalyst composition contain less than 5000 wt. ppm of alkali metals as determined by XRF based on the total weight of the one or more zeolites before the step of steaming; preferably, below 2500 wt. ppm, more preferably below 1000 wt. ppm.

For example, said one or more zeolites of the catalyst composition contains less than 5000 wt. ppm of alkaline earth metals as determined by XRF based on the total weight of the one or more zeolites before the step of steaming; preferably, below 2500 wt. ppm; more preferably, below 1000 wt. ppm. However, the final catalyst composition may contain a higher amount of alkaline earth metals as a component of the binder (e.g. $Ca_3(PO_4)_2$). So, additional traces of these metals may be present on the catalyst as impurities from the binder.

For example, said one or more zeolites of the catalyst composition contains less than 5000 wt. ppm of lanthanides as determined by XRF based on the total weight of the one or more zeolites before the step of steaming; preferably, below 2500 wt. ppm; more preferably, below 1000 wt. ppm.

For example, said one or more zeolites of the catalyst composition contains less than 5000 wt. ppm of rare earth elements based on the total weight of the one or more zeolites before the step of steaming; preferably, below 2500 wt. ppm; more preferably, below 1000 wt. ppm.

With preference, one or more of the following embodiments can be used to better define the zeolites used in the catalyst composition of the process:

- The one or more zeolites have a crystal size below 2000 nm, as determined by scanning electron microscopy (SEM), preferentially below 1750 nm, more preferentially below 1500 nm, even more preferentially below 1250 nm or below 1000 nm.
- The one or more zeolites have a crystal size of at least 10 nm as determined by scanning electron microscopy (SEM), for example of at least 50 nm, or at least 100 nm, or at least 200 nm, or at least 400 nm or at least 600 nm.
- The one or more zeolites comprising at least one 10-membered ring channel, with crystal size below 2000 nm, have a Si/Al molar ratio in the framework of the zeolite ranging from 10 to 1500 as determined by TPD after the step of steaming; preferably ranging from 80 to 1200; more preferably ranging from 150 to 1100 and most preferably from 800 to 1000.
- The one or more zeolites have a Si/Al molar ratio in the framework of the zeolite of at least 80 as determined by TPD after the step of steaming; with preference, of at least 150.
- The one or more zeolites have a Si/Al molar ratio in the framework of the zeolite ranging from 80 to 1500 as determined by TPD after the step of steaming; preferably ranging from 150 to 1200; more preferably ranging from 400 to 1100 and most preferably from 800 to 1000.
- The one or more zeolites are dealuminated with an organic acid solution or with an inorganic solution.
- The one or more zeolites in the catalyst composition are one or more selected from the group of MFI, MEL, FER, MTT, MVWV, TON, EUO and MRE families.
- The one or more zeolites in the catalyst composition are selected from the group of MFI, MEL, FER, MTT, MVWV, TON, EUO and MRE families and have a Si/Al molar ratio in the framework of the zeolite of at least 80 as determined by TPD after the step of steaming, with preference of at least 150.
- The one or more zeolites are selected from the MFI family.
- The one or more zeolites are or comprise MFI zeolites; with preference, with a Si/Al molar ratio in the framework of the zeolite of at least 80 as determined by TPD after the step of steaming.
- The one or more zeolites are zeolites selected from the silicalites from the MFI family and/or silicalites from the MEL family; preferably, with a Si/Al molar ratio in the framework of the zeolite of at least 80 as determined by TPD after the step of steaming; more preferably, with a Si/Al molar ratio of at least 150.
- The one or more zeolites are selected from the list comprising ZSM-5, silicalites from the MFI family, boralite C, TS-1, ZSM-11, silicalites from the MEL family, boralite D, TS-2, SSZ-46, ferrierite, FU-9, ZSM-35, ZSM-23, MCM-22, PSH-3, ITQ-1, MCM-49, ZSM-22, Theta-1, NU-10, ZSM-50, EU-1 and ZSM-48; preferably with a Si/Al molar ratio in the framework of the zeolite of at least 80 as determined by TPD after the step of steaming; more preferably, with a Si/Al molar ratio in the framework of the zeolite of at least 150.
- The one or more zeolites in the catalyst composition are MFI zeolites and are subjected to a step of steaming before step (c) followed by modification with phosphorous; with preference, the one or more zeolites are ZSM-5.
- The one or more zeolites in the catalyst composition are modified with phosphorus.
- At least 50 wt. % of said one or more zeolites are in their hydrogen form as based on the total weight of the zeolites.

With preference, one or more of the following embodiments can be used to better define the catalyst composition used in the process:

- The catalyst composition comprises at least 60 wt. % of one or more zeolites comprising at least one acid 10-membered ring channel, preferably at least 70 wt. %, more preferably at least 80 wt. %, even more preferably at least 90 wt. % and most preferably 100 wt. %.
- The one or more zeolites have weak Brønsted acid sites in a concentration inferior to 40 µmol/g-cat and strong Brønsted acid sites in a concentration superior to 40 µmol/g-cat as determined by $NH_3$— Temperature Programmed Desorption.
- The one or more zeolites have Brønsted acid sites in a concentration inferior to 100 µmol/g-cat as determined by $NH_3$— Temperature Programmed Desorption, preferentially inferior to 90 µmol/g-cat, more preferentially inferior to 80 µmol/g-cat.
- The catalyst composition further comprises at least 0.1 wt. % of phosphorous based on the total weight of the catalyst composition, preferentially with at least 0.5 wt. % of phosphorous, more preferentially with at least 1.0 wt. % of phosphorous, even more preferentially with at least 1.5 wt. % of phosphorous. In a preferred embodiment, the catalyst composition is modified with 2.3 wt. % of phosphorous.
- The catalyst composition is modified with phosphoric acid; and/or the catalyst composition comprises phosphoric acid and magnesium nitrate.
- The catalyst composition comprises at least 0.1 wt. % of phosphorous based on the total weight of the catalyst composition and is blended with at least one metal-containing material; with preference, the at least one metal-containing material is an alkaline earth metal-containing material which comprises at least one alkaline earth metal selected from beryllium, magnesium, calcium, strontium, barium and any mixtures thereof; and/or the at least one metal-containing material has an anion selected from the group of oxides, silicates, aluminates, titanates, phosphates, borates and borosilicates;
- The catalyst composition comprises at least 0.1 wt. % of phosphorous based on the total weight of the catalyst composition and is blended with at least one metal-containing material; wherein the at least one metal-containing material is one or more selected from an alkaline earth metal-containing material, magnesium nitrate, and a cerium-containing material.
- The one or more zeolites are doped with a phosphorus-containing material before or after the steaming step, so as to form one or more phosphate zeolites.

The one or more zeolites are one or more phosphate zeolites and are further subjected to a steaming step.

The catalyst composition comprises between 0.1 wt. % and 7.0 wt. % of a phosphorus-containing material as based on the total weight of the catalyst composition, preferably between 0.3 wt. % and 4.5 wt. %, preferentially between 0.5 wt. % and 4.0 wt. %, more preferentially 2.0 wt. %.

The one or more zeolites are doped with at least one phosphorus-containing material and with at least one alkaline earth metal-containing material, preferably at least one alkaline earth metal-containing material is selected from at least one magnesium-containing material and/or at least one calcium-containing material.

The binder is selected from silica, clays, calcium phosphates, magnesium phosphates, and mullite. Most preferentially, the binder is silica.

The binder is free of aluminium compounds; i.e. the binder does not contain aluminium compounds, such as alumina.

The binder is present in an amount of at least 10 wt. % as based on the total weight of the catalyst composition; preferably in an amount of at least 20 wt. %, most preferably in an amount of 30 wt. %, even more preferably in an amount of at least 40 wt. %, and most preferably in an amount of at least 50 wt. %.

In a preferred embodiment, the catalyst composition is calcinated before said step (c) of contacting the feedstream; with preference, the catalyst composition is calcined at a temperature of at least 400° C.

With preference, one or more of the following embodiments can be used to better define the step (a) of the process:

The one or more alkyl halides in the feedstream of step (a) comprise one or more monohalo-alkyl, preferably methyl bromide.

The one or more alkyl halides in the feedstream of step (a) comprise one or more monohalo-akly with at most 10 wt. % of polyhalo-alkyl, such as dihalo-alkyl, trihalo-alkyl and/or tetrahalo-alkyl.

The one or more alkyl halides in the feedstream of step (a) comprise a mixture of one or more selected from monohalo-alkyl, dihalo-alkyl, trihalo-alkyl and/or tetrahalo-alkyl; with preference the mixture comprises monohalo-alkyl in an amount of at least 90 wt. % of said mixture.

The alkyl of said one or more alkyl halides is methyl, ethyl, propyl and/or any mixture thereof.

The halogen of said one or more alkyl halides is selected from fluorine, chlorine, bromine, iodine and/or any mixture thereof.

The diluent in the feedstream comprises one or more of hydrogen halides, steam, C1-C4 alkanes, $CO_2$, or $N_2$, preferentially $N_2$ The one or more alkyl halides are substantially free of oxygenates, with preference free of methanol, ethanol and/or propanol.

The one or more alkyl halides are diluted into $N_2$, hydrogen halides, $H_2$, $CO_2$, non-converted $CH_4$, CO, $C_2H_6$, $O_3H_8$, and/or $C_4H_{10}$, more preferably gaseous nitrogen.

With preference, one or more of the following embodiments can be used to better define the step of steaming of the process:

The one or more steamed zeolites of the catalyst composition are leached with an organic or inorganic acid solution, before the step (c). The steaming and the leaching of the catalyst composition are performed subsequently, the steaming step being conducted first.

Said step of steaming is carried out at a temperature ranging between 300° C. and 800° C., preferentially ranging between 400° C. and 750° C.

Said step of steaming is carried out at a partial pressure of the steam ranging between 0.01 kPa and 20 kPa, preferentially between 0.5 kPa and 1.5 kPa.

Said step of steaming is followed by an extraction step, with preference with a monoprotic acid selected from HCl, $HNO_3$, HBr, acetic acid or formic acid.

Said step of steaming is followed by an extraction step, with preference with a complexing agent or with an aqueous complexing agent.

Said step of steaming is followed by an extraction step and by a calcination step; with preference, said calcination step is carried out in a steam-free atmosphere at a temperature ranging between 550° C. and 700° C., more preferably at a temperature ranging between 600° C. and 650° C.

Said step of steaming is followed by a calcination step; with preference, said calcination step is carried out in a steam-free atmosphere at a temperature ranging between 550° C. and 700° C., more preferably at a temperature ranging between 600° C. and 650° C.

Said step of steaming is followed by a step of modification of the steamed catalyst by phosphorous.

In an embodiment, said step of steaming is followed by a step of modification of the steamed catalyst by phosphorous under reduced or atmospheric pressure, preferentially at a temperature from 10 to 400° C., more preferentially at a temperature from 50° C. to 350° C., even more preferentially at a temperature from 100° C. to 300° C. With preference:

The source of phosphorous in the modification step of the steamed catalyst is mixed in an aqueous or a non-aqueous medium.

The source of phosphorous in the modification step of the steamed catalyst is mixed in a non-aqueous medium selected from the group of ethanol, methanol and/or other alcohols.

The source of phosphorous is phosphoric acid, preferably a solution of phosphoric acid.

The modification step of the steamed catalyst is followed by a calcination step; with preference, said calcination step is carried out in a steam-free atmosphere at a temperature ranging between 550° C. and 700° C., more preferably at a temperature ranging between 600° C. and 650° C.

The modification step of the steamed catalyst is followed by a further step of steaming, preferentially at a steam partial pressure comprised between 0.1 and 1.0 kPa and/or at a temperature comprised between 550 and 750° C. and/or for a period of from 0.5 to 10 hours.

The modification step of the steamed catalyst is followed by a calcination step and by a further step of steaming, preferentially at a steam partial pressure comprised between 0.1 and 1.0 kPa and/or at a temperature comprised between 550° C. and 750° C. and/or for a period of from 0.5 to 10 hours.

With preference, one or more of the following embodiments can be used to better define the step (c) of the process:

Step (c) has a conversion rate of at least 20% of the one or more alkyl halides into hydrocarbons; with preference, of at least 30%.

The reaction conditions of step (c) include a reaction temperature ranging from 150° C. to 380° C., preferably ranging from 250° C. to 350° C.; more preferably ranging from 260° C. to 340° C.; even more preferably ranging from 280° C. to 320° C., most preferably at a temperature of 300° C.

The reaction conditions of step (c) include a weight hourly space velocity of said one or more alkyl halides comprised between 0.1 h$^{-1}$ and 100 h$^{-1}$, preferably comprised between 1.0 h$^{-1}$ and 15 h$^{-1}$, more preferably comprised between 1.5 h$^{-1}$ and 10 h$^{-1}$, even more preferably comprised between 2.0 h$^{-1}$ and 6.0 h$^{-1}$.

The reaction conditions of step (c) include a partial pressure of said one or more alkyl halides ranging from 10 kPa to 500 kPa, preferably ranging from 20 kPa to 300 kPa, more preferably ranging from 50 kPa to 200 kPa.

The step (c) of contacting the feedstream with the catalyst composition is followed by a step (d) of recovering an effluent comprising acyclic C3-C6 olefins, one or more hydrogen halides, unreacted one or more alkyl halides, alkane and higher hydrocarbons and optionally said diluent; wherein the selectivity to acyclic C3-C6 olefins is of at least 25%; with preference, of at least 30%.

According to a second aspect, the disclosure provides the use of a catalyst composition in a process according to the first aspect, remarkable in that said catalyst composition comprises one or more zeolites and a binder, wherein said one or more zeolites comprise at least one 10-membered ring channel, and further wherein said catalyst composition is steamed before use.

DETAILED DESCRIPTION OF THE DISCLOSURE

Figure 1:
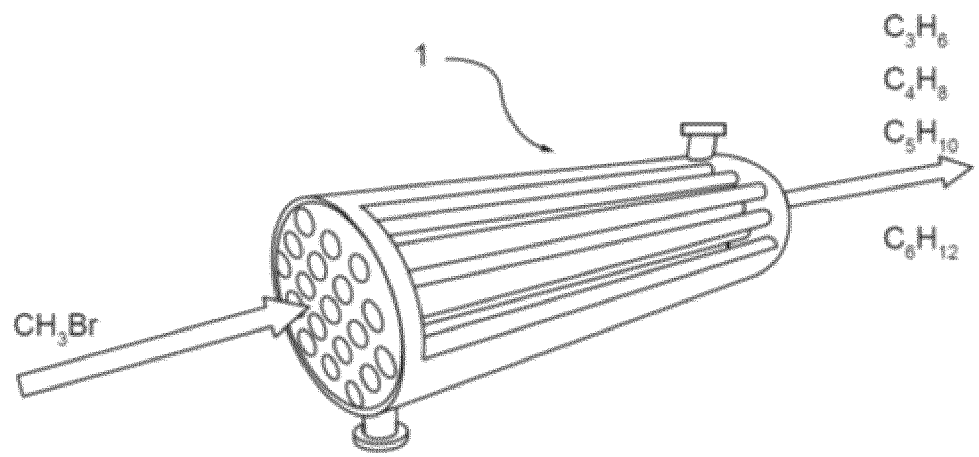
FIG. 1 schematically illustrates a fixed-bed tubular reactor in which the catalytical reaction of the present disclosure is carried out.

For the purpose of the disclosure, the following definitions are given:

Zeolite codes (e.g., CHA . . . ) are defined according to the "*Atlas of Zeolite Framework Types*", 6$^{th}$ revised edition, 2007, Elsevier, to which the present application also makes reference.

The terms "alkane" or "alkanes" as used herein describe acyclic branched or unbranched hydrocarbons having the general formula $C_nH_{2n+2}$, and therefore consisting entirely of hydrogen atoms and saturated carbon atoms; see e.g. IUPAC. Compendium of Chemical Terminology, 2nd ed. (1997). The term "alkanes" accordingly describes unbranched alkanes ("normal-paraffins" or "n-paraffins" or "n-alkanes") and branched alkanes ("iso-paraffins" or "iso-alkanes") but excludes naphthenes (cycloalkanes).

The term "aromatic hydrocarbons" or "aromatics" relates to cyclically conjugated hydrocarbon with a stability (due to derealization) that is significantly greater than that of a hypothetical localized structure (e.g. Kekule structure). The most common method for determining aromaticity of a given hydrocarbon is the observation of diatropicity in the $^1$H NMR spectrum.

The terms "olefin" or "alkene" as used herein relate to an unsaturated hydrocarbon compound containing at least one carbon-carbon double bond.

The terms "mono-olefin" as used herein relates to an unsaturated hydrocarbon compound containing one single carbon-carbon double bond.

The SAR of one or more zeolites refers to the silica to alumina molar ratio of said one or more zeolites. SAR is determined by NH$_3$— Temperature Programmed Desorption.

As used herein, the term "C# hydrocarbons", wherein "#" is a positive integer, is meant to describe all hydrocarbons having # carbon atoms. C# hydrocarbons are sometimes indicated as just C#. Moreover, the term "C#+ hydrocarbons" is meant to describe all hydrocarbon molecules having # or more carbon atoms. Accordingly, the expression "C5+ hydrocarbons" is meant to describe a mixture of hydrocarbons having 5 or more carbon atoms.

The symbol "=" in the term "C#=hydrocarbon" indicates that the hydrocarbon concerned is an olefin or an alkene, the notation "=" symbolizing the carbon-carbon double bond. For instance, "C6=" stands for "C6 olefin", or for "olefins comprising 6 carbon atoms".

The term "steam" is used to refer to water in the gas phase, which is formed when water boils.

The term "alkali metal" refers to an element classified as an element from group 1 of the periodic table of elements (or group IA), excluding hydrogen. According to this definition, the alkali metals are Li, Na, K, Rb, Cs and Fr.

The term "alkaline earth metal" refers to an element classified as an element from group 2 of the periodic table of elements (or group IIA). According to this definition, the alkaline earth metals are Be, Mg, Ca, Sr, Ba and Ra.

The term "transition metal" refers to an element whose atom has a partially filled d sub-shell, or which can give rise to cations with an incomplete d sub-shell (IUPAC definition). According to this definition, the transition metals are Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ac, Rf, db, Sg, Bh, Hs, Mt, Ds, Rg, and Cn. The term "transition metal" includes the group 12 elements i.e. Zn, Cd and Hg.

The term "rare earth elements" refer to the fifteen lanthanides, as well as scandium and yttrium. The 17 rare-earth elements are cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y).

The term "lanthanides" corresponds to the 15 metallic chemical elements with atomic numbers 57-71, from lanthanum through lutetium.

The yield to particular chemical compounds is determined as the mathematical product between the selectivity to said particular chemical compounds and the conversion rate of the chemical reaction. The mathematical product is expressed as a percentage.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The particular features, structures, characteristics or embodiments may be combined in any suitable manner, as would be apparent to a person skilled in the art from this disclosure, in one or more embodiments.

The disclosure provides a process for converting one or more alkyl halides to acyclic C3-C6 olefins, preferentially a process for converting one or more alkyl halides to acyclic C3-C6 mono-olefins, said process comprising the following steps:
a) providing a feedstream comprising one or more alkyl halides; optionally, diluted in at least one diluent;
b) providing a catalyst composition; and
c) contacting said feedstream with said catalyst composition under reaction conditions;
according to the disclosure, said process further comprises a step of steaming said catalyst composition before the step (c) and said catalyst composition comprises one or more zeolites and a binder, wherein said one or more zeolites comprise at least one 10-membered ring channel, and contain less than 5000 wt. ppm of transition metals as determined by XRF based on the total weight of the one or more zeolites; and further wherein said one or more zeolites of the catalyst composition have a Si/Al molar ratio in the framework of the zeolite of at least 10 as determined by TPD before the step of steaming.

The Catalyst Composition of the Present Disclosure

It is preferred that the one or more zeolites, namely the one or more zeolites before the step of steaming, or the one or more non-steamed zeolites, do not contain any alkali metals since these metals may significantly reduce catalyst activity and neutralize acid sites. In a preferred embodiment, said one or more zeolites contain less than 1000 wt. ppm of alkali metals as determined by XRF based on the total weight of the one or more zeolites.

It is preferred that the one or more zeolites, namely the one or more zeolites before the step of steaming, do not contain any alkaline earth metal since these metals may impact the steam dealumination process and retain halogen after the reaction. The retained halogen will be released during the regeneration and irreversibly deactivate zeolites.

In the case where the one or more zeolites are doped with at least one phosphorus-containing material and at least one alkaline earth metal-containing material, the alkaline earth metal is strongly bound with the phosphorous and is less prone to the formation of halides.

It is preferred that the catalyst composition does not contain any transition metal since this leads to a completely distinct reactivity resulting in coke formation. This is why the catalyst composition is devoid of any transition metal. This means that the content of the transition metals is below 5000 wt. ppm as determined by XRF in the one or more zeolites based on the total weight of the one or more zeolites, preferably below 2500 wt. ppm as determined by XRF in the one or more zeolites. Traces of these metals may be present on the catalyst as impurities from the binder.

For example, said one or more zeolites of the catalyst composition are free of gallium and/or cerium. For example, said one or more zeolites of the catalyst composition are free of zinc. In a more general way, the one or more zeolites of the catalyst composition are free of transition metals, and/or are free of rare earth elements, and/or are free of lanthanides, and/or are free of alkaline earth metals, and/or are free of alkali metals.

In a preferred embodiment, said one or more zeolites contain less than 1000 wt. ppm of alkali metals as determined by XRF based on the total weight of the one or more zeolites and/or less than 2500 wt. ppm of transition metals as determined by XRF based on the total weight of the one or more zeolites.

For example, said one or more zeolites of the catalyst composition contain less than 5000 wt. ppm of alkali metals as determined by XRF based on the total weight of the one or more zeolites before the step of steaming; preferably, below 2500 wt. ppm, more preferably below 1000 wt. ppm.

For example, said one or more zeolites of the catalyst composition contains less than 5000 wt. ppm of alkaline earth metals as determined by XRF based on the total weight of the one or more zeolites before the step of steaming; preferably, below 2500 wt. ppm; more preferably, below 1000 wt. ppm. However, the final catalyst composition may contain a higher amount of alkaline earth metals as a component of the binder (e.g. $Ca_3(PO_4)_2$). So, additional traces of these metals may be present on the catalyst as impurities from the binder.

For example, said one or more zeolites of the catalyst composition contains less than 5000 wt. ppm of lanthanides as determined by XRF based on the total weight of the one or more zeolites before the step of steaming; preferably, below 2500 wt. ppm; more preferably, below 1000 wt. ppm.

For example, said one or more zeolites of the catalyst composition contains less than 5000 wt. ppm of rare earth elements as determined by XRF based on the total weight of the one or more zeolites before the step of steaming; preferably, below 2500 wt. ppm; more preferably, below 1000 wt. ppm.

The one or more zeolites comprise at least one acid 10-membered ring channel; with preference, the one or more zeolites are one or more selected from the list comprising MFI, MEL, FER, MTT, MVWV, TON, EUO and MRE families, preferentially from the MFI family and/or from the MEL family. These zeolites or molecular sieves are aluminosilicate catalysts that have a chemical structure that is largely different from the chemical structure of the aluminophosphate and silicoaluminophosphate molecular sieves.

With preference, the zeolites from the MFI family is selected from ZSM-5, silicalites, boralite C, or TS-1. Preferentially, the zeolites are silicalites from the MFI family or ZSM-5, more preferentially the zeolites are silicalites from the MFI family. The zeolites from the MEL family is, preferentially, selected from ZSM-1, silicalites, boralite D, TS-2, or SSZ-46. Preferentially, the zeolites are silicalites from the MEL family. The zeolites from the FER family are, preferentially, selected from ferrierite, FU-9 or ZSM-35. The zeolites from the MTT family is, preferentially, ZSM-23. The zeolites from the MVWV family are, preferentially, selected from MCM-22, PSH-3, ITQ-1, or MCM-49. The zeolites from the TON family are, preferentially, selected from ZSM-22, Theta-1, or NU-10. The zeolites from the EUO family are, preferentially, selected from ZSM-50 or EU-1. The zeolites from the MRE family are, preferentially, ZSM-48.

Therefore, in a preferred embodiment, the catalyst composition comprises one or more zeolites with at least acid 10-membered ring channel.

Advantageously, the one or more zeolites have a crystal size below 2000 nm as determined by scanning electron microscopy (SEM), preferentially below 1750 nm, more preferentially below 1500 nm and even more preferentially below 1250 nm or below 1000 nm. The fact that the one or more zeolites have a small size allows for better accessibility of the reactants to the catalyst, which renders the catalyst composition more active.

Advantageously, the one or more zeolites have a crystal size of at least 10 nm as determined by scanning electron microscopy (SEM), for example of at least 50 nm, or at least 100 nm, or at least 200 nm, or at least 400 nm or at least 600 nm.

For example, the one or more zeolites have an average crystal size ranging from 10 nm to below 2000 nm as determined by scanning electron microscopy (SEM); for example, ranging from 50 nm to below 1750 nm; for example, ranging from 100 nm to below 1500 nm; and for example, ranging from 200 nm to below 1250 nm; for example, ranging from 400 nm below 1000 nm; for example, ranging from 600 nm to below 800 nm.

The catalyst composition comprising the one or more zeolites is steamed before the step (c) of contacting said feedstream with the said catalyst composition under reaction conditions so as to obtain a higher Si/Al molar ratio in the framework of the zeolite relative to the non-steamed one or more zeolites.

Advantageously, the one or more zeolites are selected from the list comprising ZSM-5, silicalites from the MFI family, boralite C, TS-1, ZSM-11, silicalites from the MEL family, boralite D, TS-2, SSZ-46, ferrierite, FU-9, ZSM-35, ZSM-23, MCM-22, PSH-3, ITQ-1, MCM-49, ZSM-22, Theta-1, NU-10, ZSM-50, EU-1 and ZSM-48, said one or more zeolites having a Si/Al molar ratio in the framework of the zeolite of at least 10 as determined by TPD before the step of steaming.

Advantageously, the one or more zeolites are selected from the list comprising ZSM-5, silicalites from the MFI family, boralite C, TS-1, ZSM-11, silicalites from the MEL family, boralite D, TS-2, SSZ-46, ferrierite, FU-9, ZSM-35, ZSM-23, MCM-22, PSH-3, ITQ-1, MCM-49, ZSM-22, Theta-1, NU-10, ZSM-50, EU-1 and ZSM-48, said one or more zeolites having a Si/Al molar ratio in the framework of the zeolite of at least 80 as determined by TPD after the step of steaming, with preference of at least 150.

In a preferred embodiment, the catalyst composition comprises 3D zeolites without cages (cavities) and containing at least one 10-membered ring.

Preferably, the catalyst composition comprises at least 60 wt. % of one or more zeolites having at least one acid 10-membered ring channel, more preferably at least 70 wt. %, even more preferably at least 80 wt. % and most preferably at least 90 wt. % or 95 wt. %, or 100 wt. %.

To provide an appropriate acidity, it is preferred that the zeolites are at least partly in their hydrogen form or at least partly in their ammonia form. Preferably more than 50 wt. % of the total amount of the zeolites used are in their hydrogen form or in their ammonia form, preferably at least 80 wt. %, more preferably at least 90 wt. %, and even more preferably 100 wt. % of the zeolites are in their hydrogen form or in their ammonia form.

The one or more zeolites have weak Brønsted acid sites in a concentration inferior to 40 μmol/g-cat and strong Brønsted acid sites in a concentration superior to 40 μmol/g-cat as determined by $NH_3$-TPD. The one or more zeolites have Brønsted acid sites in a concentration inferior to 100 μmol/g-cat as determined by $NH_3$-TPD, preferentially inferior to 90 μmol/g-cat, more preferentially inferior to 80 μmol/g-cat. This can be obtained by performing a step of steaming the one or more zeolites before the contact of the catalyst composition with the feedstream.

The acidity of the zeolite catalyst was measured by $NH_3$-TPD. Generally, a temperature at which $NH_3$ is desorbed is an estimation of the strength of an acid site, i.e. higher the desorption temperature stronger is the acid site. The zeolite catalyst shows two $NH_3$-TPD peaks, a first one at 184° C. and a second at 363° C.

One or more zeolites used in the catalyst composition of the disclosure have a Si/Al molar ratio in the framework of the zeolite of at least 10 as determined by TPD before the step of steaming, The Si/Al molar ratio before the step of steaming is typically ranging from 10 to 1500 as determined by TPD; preferably ranging from 80 to 1200; more preferably ranging from 150 to 1100 and most preferably from 800 to 1000.

In fact, the formation of extra-framework Al species is known to affect the pore structure and the porosity of the zeolite. Therefore, the removal of a large fraction of Al from the lattice leads to rearrangements of Si-T (tetrahedron) atoms and hence to the generation of large voids in the structure. The presence of such pores is crucial to obtain a high catalytic activity. Moreover, less aluminium also contributes to low coke formation and to low ageing rates.

The steam treatment is conducted at elevated temperature, preferably in the range of from 300 to 800° C., more preferably in the range of from 400 to 750° C. and at a partial pressure of steam from 0.01 to 20 kPa, preferentially from 0.5 to 1.5 kPa. Preferably, the steam treatment is conducted at partial pressure of steam at least 1.5 kPa in the temperature range 300-450° C.

If the temperature is above 450° C., the steam treatment is conducted in an atmosphere comprising the steam partial pressure below 1.5 kPa. The concentration of steam in the flow is between 1 to 100%, more preferably from 5 to 20% of steam. The diluent is a gas selected from the group of $N_2$, air, natural gas, $CO_2$ or a mixture of thereof. The steam treatment is preferably carried out for a period of from 0.1 to 200 hours, more preferably from 0.2 hours to 24 hours. As stated above, the steam treatment tends to reduce the amount of tetrahedral aluminium in the crystalline silicate framework, by forming alumina. The particular effect consists in reducing the strong Brønsted external acidity of the zeolites.

One or more zeolites used in the catalyst composition of the disclosure have a Si/Al molar ratio in the framework of the zeolite of at least 80 as determined by TPD after the step of steaming, The Si/Al molar ratio in the framework of the zeolite after the step of steaming is typically ranging from 80 to 1500; preferably ranging from 150 to 1200; more preferably ranging from 400 to 1100 and most preferably from 800 to 1000.

Optionally, following the steam treatment, an extraction step is performed in order to remove the partially dislodged alumina species by leaching. The leaching is performed by a monoprotic acid selected from the HCl, $HNO_3$, HBr, acetic or formic or with a complexing agent which tends to form a soluble complex with alumina. The complexing agent is preferably in an aqueous solution thereof. The complexing agent may comprise an organic acid such as citric acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. A particularly preferred complexing agent may comprise an amine, preferably ethylene diamine tetraacetic acid (EDTA) or a salt thereof, in particular, the sodium salt thereof.

Following the step of steaming, the catalyst is advantageously thereafter calcined in absence of steam (<1% of steam) at a temperature of from 550 to 700° C. at atmospheric pressure for a period of from 0.5 to 10 hours.

Optional Modification of the Steamed Catalyst Composition with Phosphorus

Optionally, following the steaming step of the catalyst composition, said steamed catalyst composition is further modified by phosphorous under reduced or atmospheric pressure at a temperature from 10 to 400° C. A non-limiting source of phosphorus can be provided in an aqueous or non-aqueous medium.

In an embodiment, the non-limiting source of phosphorus is dissolved in anon-aqueous medium selected from the group containing ethanol, methanol or other alcohols.

The doping with a phosphorus-containing material consists of a steaming step followed by a leaching step using a solution of phosphoric acid ($H_3PO_4$) or using any acid solution containing the source of phosphorus. It is generally known by the persons in the art that steam treatment of zeolites results in aluminium that leaves the zeolite framework and resides as aluminium oxides in and outside the pores of the zeolite. This transformation is known as the dealumination of zeolites. The treatment of the steamed zeolite with an acid solution results in the dissolution of the extra-framework aluminium oxides. This transformation is known as leaching. Then the zeolite is separated, advantageously by filtration, and optionally washed. A drying step can be envisaged between the filtering and washing steps. The solution after the washing can be either separated, by way of example, by filtering from the solid or evaporated. The residual phosphorus-content is adjusted by the phosphorus concentration in the leaching solution, drying conditions, and washing procedure if any. This procedure leads to dealumination of zeolites and retention of phosphorus. Advantageously, at least 0.1 wt. % and up to 7.0 wt. % of phosphorus is retained after dealumination on zeolite. Both factors dealumination and the retention of phosphorus stabilize the lattice aluminium in the zeolitic lattice, thus avoiding further dealumination. This leads to higher hydrothermal stability, tuning of molecular sieves properties and adjustment of acid properties. The degree of dealumination can be adjusted by the steaming and leaching conditions.

The preferred techniques suitable for the modification by phosphorous are impregnation and chemical vapour deposition.

These techniques imply a minimum waste to treat and allow maintaining substantially all phosphorus on the catalyst.

In an embodiment, the phosphorus is introduced by a treatment of the catalyst in a solution containing a source of phosphorus at a temperature ranging between 25 and 100° C. for 0.1-96 h followed by filtering or evaporation.

In a preferred embodiment, the incipient wetness (IW) impregnation techniques are used. In these IW impregnation techniques, the phosphorus is introduced via impregnation using a limited amount of liquid water which is subjected to contact with the catalyst. This method is also known as dry impregnation.

Incipient wetness (IW) or incipient wetness impregnation (IWI) is a commonly used technique for the synthesis of heterogeneous catalysts. Typically, the precursor (phosphorus-containing compounds) is dissolved in an aqueous or organic solution. The volume of solution, which is used for dissolution of the precursor, is substantially the same as the pore volume of catalyst precursor containing both binder and zeolite. Then the precursor-containing solution is added to a catalyst precursor. Capillary action draws the solution into the pores. The catalyst can then be dried and calcined to drive off the volatile components within the solution, depositing the phosphorus on the catalyst surface.

The sample before impregnation can be dried or calcined. The impregnation could be performed at room or elevated temperature.

The adsorption capacity is typically measured by impregnating the dried extruded zeolite with water until the zeolite was completely wet. Weighing the zeolite before and after impregnation gives the absorption capacity according to formula (1):

$$\text{Absorption capacity}(\%) = \frac{\text{weight after impregnation} - \text{dry weight}}{\text{dry weight}} * 100 \quad (1)$$

In an embodiment, $H_3PO_4$ solution is used for impregnation.

Advantageously, a mixture of $H_3PO_4$ with their ammonium salts providing a pH of the aqueous solution higher than 2.0 is used for impregnation.

In an embodiment, the sources of phosphorus are substantially metal-free components, for example, $H_3PO_4$, ammonium phosphates or organic phosphorous-compounds. By way of example, this proportion can be below 1000 wt·ppm of the total weight of the phosphorous-containing material.

The amount of phosphorus in the catalyst can be from 0.1 to 30.0 wt. %, preferably from 0.3 to 9.0 wt. %. The amount of phosphorous on the catalyst is most preferably 2.0 wt. %.

Following the introduction of phosphorous, the catalyst is thereafter calcined and/or steamed at a steam partial pressure between 0.1 and 1 kPa at a temperature of from 550 to 750° C. at for a period of from 0.5 to 10 hours.

Steaming, in addition to trigger aluminium leaching also allows for the reduction of the number of acid sites.

The crystalline alumino-silicate oxide framework of the one or more zeolites have a portion of the aluminium that is substituted with boron and/or titanium. Preferentially, boron is used to substitute one or more aluminium atoms in the zeolite framework. Boron-substituted zeolite has a very weak acidity. The zeolite catalysts have a Si/(Al+B) molar ratio of at least 80, typically comprised between 100 and 1200, preferentially of 1000.

Optional Modification of the Phosphorous Modified Steamed Catalyst

The catalyst composition modified with a phosphorous containing-material may contain a metal-containing material, which is preferably an alkaline earth metal-containing material. However, the alkaline earth metal-containing material is spatially separated from the zeolite, in which alkaline earth metal is strongly bounded with phosphorous. The said alkaline earth metal is selected from the group of beryllium, magnesium, calcium, strontium, barium and any mixtures thereof.

The metal-containing material that can be added to a catalyst composition modified with phosphorous is advantageously in the form of alkaline earth metal salts and comprise at least one inorganic anion selected preferably from the group of oxides, silicates, aluminates, titanates, phosphates, borates and borosilicates. Suitable silicate anions include $SiO_3^{2-}$, $SiO_4^{4-}$, $Si_2O_7^{6-}$ and so on. Suitable borate anions include $BO_2^-$, $BO_3^{3-}$, $B_2O_5^{4-}$, $B_4O_7^{2-}$, $B_6O_{11}^{4-}$, $B_{10}O_{19}^{8-}$ and so on. Suitable aluminate anions include $Al_2O_4^{2-}$, $AlO_4^{5-}$, $Al_6O_{18}^{18-}$ and so on. Suitable titanate anions include $TiO_3^{2-}$, $Ti_3O_7^{2-}$, $Ti_4O_9^{2-}$, $TiO_4^{4-}$ and so on. Suitable phosphate anions include $PO_4^{3-}$, $HPO_4^{2-}$, $H_2PO_4^-$, $P_nO_{3n+1}^{(n+2)-}$ and so on. Bi-, tri- and poly-metal silicates, borates and borosilicates containing one, two or more alkaline earth metals selected from the list above can be used too. The metal salt may also comprise other anions.

Examples of suitable alkaline earth metal salts that can be added to a catalyst composition modified with phosphorous include $Mg_6Al_2CO_3(OH)_{16} \cdot 4(H_2O)$ (hydrotalcite), $Mg_2B_2O_5 \cdot H_2O$, $CaMgB_6O_{11} \cdot 6H_2O$ (hydroboracite), $Ca_2B_6O_{11} \cdot 5H_2O$ (colemanite), $Ca_4B_{10}O_{19} \cdot 7H_2O$, $Mg(BO_2) \cdot 8H_2O$, $Ca(BO_2) \cdot 2H_2O$, $BaB_6O_{10} \cdot 4H_2O$, $CaSi_6O_{17}(OH)_2$ (xonotlite), $CaMg(Si_2O_6)_x$, $Mg_2(Si_2O_6)_x$, $CaAl_2Si_2O_8$, $Mg_4Si_6O_{15}(OH)_2 \cdot 6H_2O$ (sepiolite), $(Mg,Al)_2Si_4O_{10}(OH) \cdot 4H_2O$ (palygorskite or attapulgite) and mixtures thereof.

A further example of suitable alkaline earth metals that can be added to a catalyst composition modified with phosphorous is $Mg(NO_3)_2$ (magnesium nitrate).

Before mixing with the molecular sieve, said alkaline earth metal salts may be modified by calcination, steaming, ion-exchange, impregnation, and/or phosphatation. Said alkaline earth metal salts may be an individual compound or may be a part of mixed compounds, for example, mixed with mineral, natural or chemical fertilizer.

The catalyst composition of the present disclosure modified with at least one phosphorous-containing material and at least one alkaline earth metal-containing material has for effect to increase the selectivity to olefins (i.e. acyclic C3-C6 olefins) and to decrease subsequently the rate of the alkane formation (i.e. C3-C6 alkanes).

In a preferred embodiment, the catalyst composition modified with phosphorous further comprises from 1 to 50 wt. % of hydrotalcite as based on the total weight of the catalyst composition; with preference from 5 to 25 wt. %. The hydrotalcite is of the formula $Mg_6Al_2CO_3(OH)_{16} \cdot 4(H_2O)$.

In another preferred embodiment, the one or more zeolites are doped with both at least one phosphorus-containing material and with at least one alkaline earth metal-containing material, preferably at least one magnesium-containing material and/or at least one calcium-containing material.

The Shaping of the Catalyst with a Binder

According to the disclosure, one or more zeolites are shaped with a binder, which is an inorganic material, and preferentially silica. The zeolites shaped with the binder forms a catalyst composition, and the catalyst composition of the present disclosure preferably comprises at least 10 wt. % of a binder based on the total weight of the catalyst composition and at most 40 wt. %. Typically, the catalyst composition of the present disclosure comprises between 20 wt. % and 25 wt. % of a binder as based on the total weight of the catalyst composition.

The preferred binder is selected from silica, alpha-alumina, clays, alumina phosphates, calcium phosphates, magnesium phosphates, and mullite. Most preferentially, the binder is silica.

The binder preferably does not contain any aluminium compounds, such as alumina. This is because as mentioned above the preferred catalyst for use in the disclosure is de-aluminated by steaming to increase the Si/Al molar ratio in the framework of the zeolite of the crystalline silicate. The presence of alumina in the binder, as well as the presence of hydrogen halides, may lead to the re-alumination of the zeolite. The presence of aluminium in the binder would also tend to reduce the olefins selectivity of the catalyst and to reduce the stability of the catalyst over time.

The binder is present in an amount of at least 10 wt. % as based on the total weight of the catalyst composition; preferably in an amount of at least 20 wt. %, most preferably in an amount of 30 wt. %, even more preferably in an amount of at least 40 wt. %, and most preferably in an amount of at least 50 wt. %.

Non-limiting examples of silicon sources suitable for the binder of the catalyst composition include silicates, precipitated silicas, for example, Zeosil® available from Rhodia, fumed silicas, for example, Aerosil®200 available from Degussa Inc., New York, N.Y., silicon compounds such as tetraalkyl orthosilicates, for example, tetramethyl orthosilicate (TMOS) and tetraethylorthosilicate (TEOS), colloidal silicas or aqueous suspensions thereof, for example Ludox® HS-40 available from E.I. du Pont de Nemours, Wilmington, Del., silicic acid, alkali-metal silicate, or any combination thereof.

Other suitable forms of amorphous silica include silica powders, such as Ultrasil® VN3 SP (commercially available from Degussa).

Other non-limiting examples of a suitable solid silica source are special granulated hydrophilic fumed silicas, mesoporous silica and high surface area precipitated silica SIPERNAT® from Evonik, Hi-Sil 233 EP (available from PPG Industries) and Tokusil (available from Tokuyama Asia Pacific).

In addition, suitable amorphous silica sources include silica sols, which are stable colloidal dispersions of amorphous silica particles in an aqueous or organic liquid medium, preferably water.

Non-limiting examples of commercially available silica sols include those sold under the tradenames Nyacol® (available from Nyacol Nano Technologies, Inc. or PQ Corp.), Nalco (available from Nalco Chemical Company), Ultra-Sol (available from RESI Inc), Ludox® (available from W.R. Grace Davison), NexSil™ (available from NNTI).

Many silica sols are prepared from sodium silicate and inevitably contain sodium. It is, however, found that the presence of sodium ions can cause sintering of the silica body at high temperature and/or affect catalytic performance. Therefore, if silica sols containing sodium are used, a step of ion exchange may be required in order to reduce or remove sodium. To avoid carrying out ion exchange steps, it is convenient to use silica sols that contain very little or, ideally, no detectable traces of sodium and have a pH value of less than 7. Most preferably, the silica sol used in the process is slightly acidic with or without polymeric stabilizers. Non-limiting examples of silica sols that contain no detectable traces of sodium include Bindzil® 2034D1, Levasil® 200, Nalco 1034A, Ultra-Sol 7H or NexSil™ 20A.

In some case, silica dispersion prepared with alkylammonium might be useful. Non-limiting examples of commercially low sodium silica sols stabilized by ammonia or alkylammonium cations include LUDOX® TMA (available from W.R. Grace Davison) or VP WR 8520 from Evonik.

The silica sols with higher $SiO_2$ content than 30 wt. % and even up to 50 wt. %, for example, W1250, W1836, WK341, WK7330 from Evonik are particularly preferred.

The preferred source of silicon is a silica sol or a combination of silica sol with precipitated or fumed silica.

In an embodiment, the binder is present in an amount of at least 10 wt. % as based on the total weight of the catalyst composition; preferably, in an amount of at least 20 wt. %, most preferably in an amount of 30 wt. %, even more preferably in an amount of at least 40 wt. %, and most preferably in an amount of at least 50 wt. %.

Conversion of the One or More Alkyl Halides with the Catalyst Composition of the Present Disclosure When the catalyst is ready, the catalyst is filled in a reactor, which can be a fixed bed, a fluidized bed or another suitable reactor. Preferentially, it can be a fixed-bed tubular reactor 1 as schematically shown in FIG. 1.

With preference, the catalyst is pre-activated before the step of contacting the feed. The pre-activation is actually a step of drying/calcination and is performed at high temperature, preferably between 350 and 550° C. The catalyst is preferably calcinated for at least 1 hour, preferentially for at least 6 hours. The zeolite is calcinated before the step of contacting in a nitrogen atmosphere. The step of calcination provides for a crystalline structure to the zeolite.

The process comprises the step of providing a feedstream to be contacted by the catalyst, the feedstream comprises one or more alkyl halides; optionally, diluted in at least one diluent.

In a preferred embodiment, the alkyl of said one or more alkyl halides is methyl, ethyl or propyl, preferentially methyl, and in that the halogen of said one or more alkyl halides is F, Cl, Br, or I, preferentially Br.

The alkyl halide comprised in the feedstream can optionally comprise 1, 2, 3 or 4 halogens. Advantageously, the alkyl halide comprised in the feedstream comprises 1 halogen and is a monohalo-alkyl. In this case, it is advantageous that the halide is a bromide.

The one or more alkyl halides optionally comprise up to 10 wt. % of alkyl dihalide.

With preference, the alkyl halide is methyl bromide.

In a preferred embodiment, a diluent can be added in the feed comprising said one or more alkyl halides. Said diluent can be one or more of hydrogen halides, steam, C1-C4 alkanes, $CO_2$, $N_2$ or monocyclic aromatics (e.g. benzene, toluene and/or xylene), preferentially $N_2$.

Preferably, any water precursors and any hetero-compounds, which could react with the halide derivative should be avoided.

With preference, the weight of feed flowing per unit of weight of the catalyst per hour (weight hourly space velocity, WHSV) is comprised between 0.1 $h^{-1}$ and 100 $h^{-1}$, preferentially comprised between 1.0 $h^{-1}$ and 15 $h^{-1}$. More preferably, WHSV is comprised between 1.5 $h^{-1}$ and 10 $h^{-1}$. Even more preferably, WHSV is comprised between 2.0 $h^{-1}$ and 6.0 $h^{-1}$. This means that the catalyst of the present disclosure is able to convert a weight of the feed that is superior to the amount of the catalyst present in the reactor.

In a preferred embodiment, the reaction conditions of step (c) include a reaction temperature ranging from 150° C. to 380° C., preferably ranging from 250° C. to 350° C.; more preferably ranging from 260° C. to 340° C.; even more preferably ranging from 280° C. to 320° C., most preferably at a temperature of 300° C.

The use of a relatively low temperature is advantageous due to the low thermal stability of the one or more alkyl halides, the lower corrosion activity and the lower selectivity to aromatics. In US 2008/0188701 described above, the reduction in the formation of ethylene (5.96%) has been achieved at a temperature of 450° C. with a catalyst composition comprising 50 wt. % SAPO-11 molecular sieve and 50 wt. % of alumina as a binder. As it will be demonstrated in the experimental part of the present disclosure, using one or more zeolites with a binder allows for obtaining poor ethylene formation (as less than 0.5%) at a temperature of only 280° C. In the best example, the selectivity in ethylene has been measured to be less than 0.01% at a temperature of 320° C., namely 130° C. below the temperature described in the prior art for a similar reaction (although not reaching the selectivity demonstrated in the present disclosure).

Preferably, the reaction conditions of step (c) include a pressure ranging from 10 kPa to 500 kPa, preferentially ranging from 20 kPa to 300 kPa.

In an embodiment, the step (c) of contacting the feedstream with the catalyst composition is followed by a step (d) of recovering an effluent comprising acyclic C3-C6 olefins, hydrogen halide, unreacted one or more alkyl halides, alkane and higher hydrocarbons and optionally said diluent; wherein the selectivity to acyclic C3-C6 olefins is of at least 25%; with preference, of at least 30%.

The effluent of the reactions comprises the different products that formed in the catalytical reaction (the acyclic C3-C6 olefins, the traces of C2 olefins, the alkanes, the unreacted methyl bromide, hydrogen bromide, the aromatics, and the diluent if it was employed in the reaction).

Stability studies have shown that the catalyst composition provides for a steady conversion of $CH_3Br$ into C3-C6 olefins during at least 10 hours, preferably during at least 50 hours.

A separation step can be foreseen in order to isolate the different components of the effluent. For example, the separation step can be performed by distillation.

Test and Determination Methods

The conversion of the one or more alkyl halides ($X_{RX}$) is determined according to formula (2):

$$X_{RX} = \frac{[RX]^i - [RX]^f}{[RX]^i} \times 100 \quad (2)$$

wherein $[RX]^i$ and $[RX]^f$ are the molar amount of the alkyl halide RX in the (initial) feed and in the (final) effluent (or product stream) respectively.

The selectivity in methane (C1) is determined according to formula (3):

$$S_{methane} = \frac{[CH_4]}{[CH_4] + 2[C_2H_4] + 2[C_2H_6] + 3[C_3H_6] + 3[C_3H_8] + 4[C_4H_8] + 4[C_4H_{10}] + \ldots} \times 100 \quad (3)$$

wherein the numerator is the carbon adjusted molar amount of methane and the denominator is the sum of all the carbons adjusted molar amount of all hydrocarbons in the effluent.

The selectivity in ethylene (C2=) is determined according to formula (4):

$$S_{ethylene} = \frac{2[C_2H_4]}{[CH_4] + 2[C_2H_4] + 2[C_2H_6] + 3[C_3H_6] + 3[C_3H_8] + 4[C_4H_8] + 4[C_4H_{10}] + \ldots} \times 100 \quad (4)$$

wherein the numerator is the carbon adjusted molar amount of ethylene and the denominator is the sum of all the carbons adjusted molar amount of all hydrocarbons in the effluent.

The selectivity in propylene (C3=) is determined according to formula (5):

$$S_{propylene} = \frac{3[C_3H_6]}{[CH_4] + 2[C_2H_4] + 2[C_2H_6] + 3[C_3H_6] + 3[C_3H_8] + 4[C_4H_8] + 4[C_4H_{10}] + \ldots} \times 100 \quad (5)$$

wherein the numerator is the carbon adjusted molar amount of propylene and the denominator is the sum of all the carbons adjusted molar amount of all hydrocarbons in the effluent.

Similar equations (not shown) are used for determining the selectivity in butylene, pentene, and hexene, and also for the corresponding alkanes.

The selectivity in aromatics is determined according to formula (6):

$$S_{aromatics} = \frac{6[C_6H_6] + 7[C_7H_8] + 8[C_8H_{10}]}{[CH_4] + 2[C_2H_4] + 2[C_2H_6] + 3[C_3H_6] + 3[C_3H_8] + 4[C_4H_8] + 4[C_4H_{10}] + \ldots} \times 100 \quad (6)$$

wherein the numerator is the carbon adjusted molar amount of aromatics (benzene, toluene and xylene) and the denominator is the sum of all the carbons adjusted molar amount of all hydrocarbons in the effluent.

Figure 2:
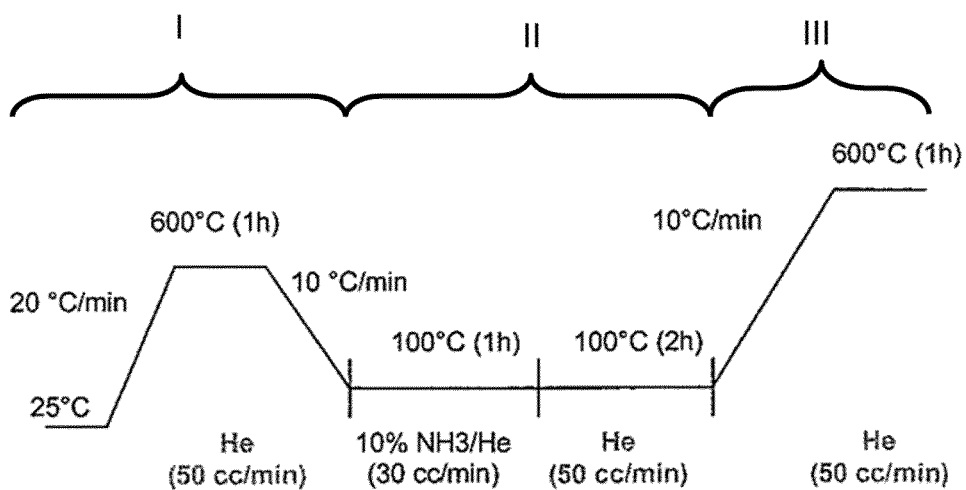
FIG. 2 shows an example of the settings of the temperature-programmed desorption (TPD) method.

Temperature Programmed Desorption (TPD) is the method of observing desorbed molecules from a surface when the surface temperature is increased. It has been performed by following the heating sequences I, II and III shows on FIG. 2, respectively corresponding to activation, saturation and analysis. In brief, in the first step (marked as I on FIG. 2), starting from room temperature (25° C.) under a flow of helium (rate 50 cc/min), the temperature has been gradually increased to 600° C. at a rate of 20° C./min. After 1 hour at 600° C., the zeolite sample is considered as being activated and the temperature is then gradually decreased to 100° C. at a rate of 10° C./min. Then, in the second step (marked as II on FIG. 2) during 3 hours, the temperature is maintained at 100° C. and in the first 1 hour, 10% of ammonia ($NH_3$) is added to the helium flow (which is decreased to 30 cc/min). The surface of the zeolite is thus saturated with the molecules of ammonia that are going to be adsorbed onto the surface. The last 2 hours of the temperature threshold at 100° C., the initial flow of helium is reinstated. Then, in the third step (marked as III in FIG. 2) the temperature is increased again to 600° C. at a rate of 10° C./min in order to desorb the ammonia. The sample is maintained at 600° C. for an additional one hour. It is highlighted that the skilled person could use different parameters (time, temperature, flow rate, carrier gas) to perform the method. The measurement of the amount of ammonia using a thermal conductivity detector allows to recognize the different adsorption conditions of the ammonia onto the zeolite and allows for obtaining a description of the surface of the zeolite, such as the number of acid sites.

For the measurement of the amount of ammonia in the zeolite sample, the sample is dried, corrected to loss of ignition at 200° C.

In order to determine the Si/Al molar ratio of the zeolites sample by $NH_3$-TPD method, the measurement of the amount of aluminium in the framework is based on the assumption that one $NH_3$ molecule interacts with one Brønsted or Lewis acid site. As the sample of zeolite is saturated at 100° C. with dry $NH_3$, all kind of physisorption (physical sorption on sites non-linked with Al in the framework) is avoided to limit the polydentate interactions (interaction of the acid sites with several molecules of ammonia). Subsequently, only the strongly adsorbed $NH_3$ molecules on the acid sites are quantified. This means that by the measurement of the amount of the strongly adsorbed $NH_3$ in TPD, it is possible to obtain the amount of the acid sites linked with Al in the framework of zeolite. In general, one atom of aluminum in the framework of zeolite generates one acid site. The number of moles (n) of $NH_3$ consumed thus corresponds to the amount of Al atoms, as determined by the following equation:

$n(Al_2O_3) = n(NH_3)/2$ [mol].

The rest would correspond to $SiO_2$, as calculated according to the following equation when the mass of the dried zeolite sample is 1 g:

$n(SiO_2) = (1[g] - Mr(Al_2O_3) * n(NH_3)/2)/Mr(SiO_2)$, Mr standing for molecular mass.

The metal content was determined by X-ray fluorescence (XRF) spectroscopy using an Orbis Micro-EDXRF spectrometer equipped with a Rh source (15 kV, 500 µA) and a silicon drift detector.

Gas chromatography experiments were carried out to determine quantitatively the selectivity of the reaction. It was performed on a silica BOND column (60 m×0.32 mm) using Agilent operated by ChemStation software.

The Si/Al atomic ratio corresponds to the amount of $SiO_2$ divided by the amount of $Al_2O_3$ taking into account the fact there are two atoms of aluminium for one atom of silicon. The silica to alumina ratio (also stated as SAR) corresponds to the amount of $SiO_2$ divided by the amount of $Al_2O_3$ notwithstanding the proportion of the Si atoms over the Al atoms in the chemical formula of the zeolite. Therefore, the value of the SAR always corresponds to twice the value of the Si/Al atomic ratio.

EXAMPLES

The embodiments of the present disclosure will be better understood by looking at the different examples below.

Example 1

A sample of commercial zeolite CBV28014 from Zeolyst (Si/Al atomic ratio of 140), ZSM-5, was shaped with a silica binder in a ratio 80:20. The extruded sample was calcined for 2 h at 600° C. followed by steaming at 750° C. for 1 h in 50% steam. A catalyst composition comprising steamed and acidified ZSM-5 to form a silicalite from the MFI family with $SiO_2$ binder, showing the final Brønsted acid sites concentration of 81 µmol/g-cat (measured by $TPD-NH_3$), was thus prepared.

Figure 3:
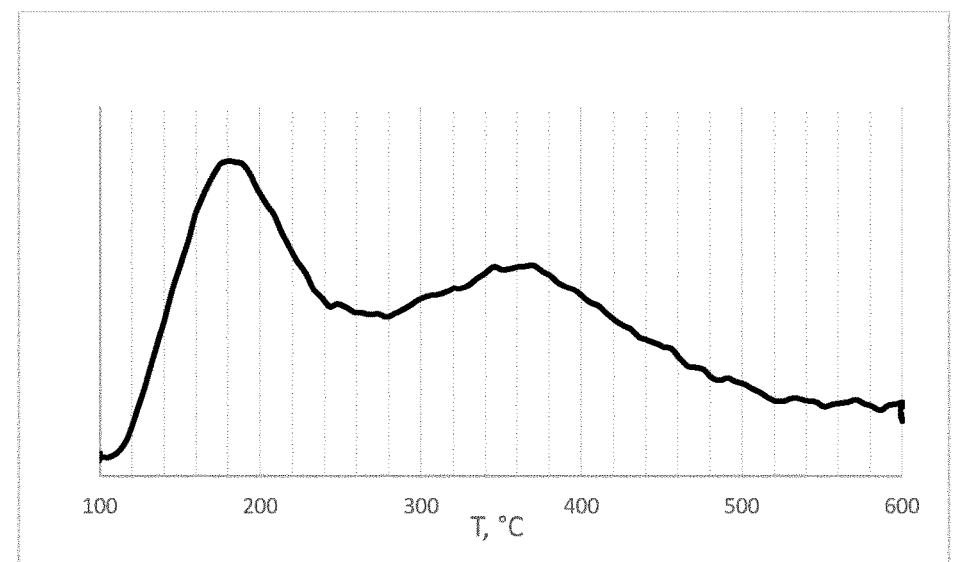
FIG. 3 shows the NH$_3$-TPD profile of the catalyst according to the disclosure.

The particulars of said catalyst composition, as determined by the TPD (Temperature Programmed Desorption) test, show that the acid site density (µmol/g-cat), measured from the amount of $NH_3$ desorbed, is of 32 µmol/g-cat for the first peak measured at 184° C. and 49 µmol/g-cat for the second peak measured at 363° C. (see FIG. 3 which plotted the thermal conductivity detector signal in function of the temperature). Therefore, the Brønsted acid sites are present in a concentration of 81 µmol/g-cat.

The catalyst was used for $CH_3Br$ conversion in a fixed-bed tubular reactor in a form of 35-45 mesh at a temperature of 280° C. for a period of 48 h or longer. In the test, a fresh load of the seized catalyst of 10 mL (i.e. 6.3 g) was loaded in a reactor (11 mm inner diameter) and the catalyst was preactivated in an $N_2$ flow at 525° C. for 6 h. Then, the temperature was decreased to 280° C. and pure $N_2$ flow was replaced with the flow of $N_2/CH_3Br$ 10/1 mol. with WHSV of $CH_3Br$/catalyst of 1.6 $h^{-1}$. The overall reactor pressure was 2 barg during the test run.

The results are reported in table 1 and compared to prior art results given in US2016/0200642.

TABLE 1

Conversion and selectivity results: example 1 vs. prior art

| Catalyst | Example 1 silicalite[#] with $SiO_2$ binder | Comparative example 1[(1)] HZMS-5 | Comparative example 2[(1)] silicalite[#] |
|---|---|---|---|
| SAR[†] | >150 | 30 | 1192 |
| Temperature (° C.) | 280 | 350 | 350 |
| Pressure | 2 barg | 0.2 barg | 0.2 barg |
| WHSV ($h^{-1}$) | 1.6 | 0.9 | 0.9 |
| $N_2/CH_3Br$ (mol/mol) | 10/1 | — | — |
| $N_2/CH_3Cl$ (mol/mol) | — | 4/1 | 4/1 |
| Partial pressure of $CH_3X$ | 0.27 bar | 0.24 bar | 0.24 bar |
| Products | Selectivity (%) | | |
| methane | <0.05 | n.d. | n.d. |
| ethane | <0.01 | 66.7[(2)] | 0 |
| C3 | <0.5 | | |
| C4 | 7.2 | | |
| C5 | <0.01 | 2.4[(3)] | 7.4 |
| C6 paraffins | 0.8 | | |
| C6= | 25.5 | | |
| C5= | 37.7 | | |
| C4= | 10.8 | 6.2 | 21.7 |
| C3= (propylene) | 7.9 | 2.2 | 60.2 |
| Bromides | 0.3 | n.d. | n.d. |
| Aromatics | 2.1 | 17.3 | 0 |
| C2= (ethylene) | <0.5 | 3 | 6.5 |
| Total selectivity to alkanes | <8.57 | <69.1 | <7.4 |
| Conversion | >99[(4)] | 96.6[(4)] | 8.6[(4)] |
| | Yield (%) | | |
| Yield of acyclic C3-C6 olefins | 81.1 | <10.4 | <7.7 |
| Yield of ethylene | <0.5 | 2.9 | 0.6 |
| Yield of aromatics | 2.1 | 16.7 | 0 |

[#]silicalite from the MFI family
[†]as defined from TPD measurement
[(1)]Comparative Example 1 corresponds to example 1 of US2016/0200642 and comparative example 2 corresponds to example 8 of US2016/0200642.
[(2)]data for C2-C4 alkanes
[(3)]data for C5+ hydrocarbons
[(4)]Conversion measured after 20 hours on stream (1) Comparative Example 1 corresponds to example 1 of US2016/0200642 and comparative example 2 corresponds to example 8 of US2016/0200642.

(2) data for C2-C4 alkanes (3) data for C5+ hydrocarbons (4) Conversion measured after 20 hours on stream From the results, it can be seen that the catalyst composition comprising silicalites from the MFI family combined to a $SiO_2$ binder and the process of the disclosure wherein the catalyst composition is steamed before use achieve a high yield to acyclic C3-C6 olefins whereas, in the prior art, such a yield is quite low. In addition, the disclosure allows a low yield to ethylene (<0.5%) as well as a low yield to aromatics compounds (<15%).

Example 2

A sample of zeolite ZSM-5 (CBV2314 from Zeolyst) (Si/Al atomic ratio of about 12) in $NH_4$-form was shaped with a silica binder in a ratio 80:20. The extruded sample was calcined for 2 h at 600° C. followed by steaming at 600° C. for 2 h in 50% steam. Then the sample was incipient wetness impregnated with an aqueous solution containing phosphoric acid to introduce 2.3 wt. % of phosphorous. The impregnated solid was dried for 16 h at 110° C. and steamed at 750° C. for 1 h in 100% of steam.

The results are reported in table 2.

Example 3

The sample of catalyst from Example 1 was modified by impregnation with phosphoric acid, $H_3PO_4$, and magnesium nitrate, $Mg(NO_3)_2$ and utilized as a catalyst for $CH_3Br$ conversion in a fixed-bed tubular reactor at a temperature of 320° C. for a period of 48 h or longer. For the catalytic test, the powder was pressed, then crushed and seized between 35-45 mesh screens. In the test, a fresh load of the seized catalyst of 10 mL (i.e. 6.6 g) was loaded in a reactor (11 mm inner diameter) and the catalyst was pre-activated in an $N_2$ flow at 525° C. for 6 h. Then, the temperature was decreased to 320° C. and pure $N_2$ flow was replaced with the flow of $N_2/CH_3Br$ 10/3 mol/mol with WHSV of $CH_3Br$/catalyst of 5 $h^{-1}$. The reactor pressure was 2 barg during the test run.

The results are reported in table 2.

TABLE 2

Conversion and selectivity results: examples 2 and 3

| Catalyst | Example 2 P-Silicalite# with $SiO_2$ binder | Example 3 Mg—P-Silicalite# with $SiO_2$ binder |
|---|---|---|
| SAR† | >150 | >150 |
| Temperature (° C.) | 280 | 320 |
| Pressure (barg) | 2 | 2 |
| WHSV ($h^{-1}$) | 5 | 5 |
| $N_2/CH_3Br$ (mol/mol) | 10/3 | 10/3 |
| Product | Selectivity (%) | |
| methane | <0.1 | <0.1 |
| ethane | <0.01 | <0.01 |
| C3 | <0.1 | 0.4 |
| C4 | 5.8 | 2.6 |
| C5 | 0.6 | 0.3 |
| C6 paraffins | 0.5 | 0.3 |
| Total selectivity to alkane | <7.11 | <3.71 |
| ethylene | <0.01 | <0.1 |
| C3= (propylene) | 16.1 | 19.9 |
| C4= | 24.7 | 28.1 |
| C5= | 14.6 | 14.7 |
| C6= | 18.3 | 21.7 |
| Aromatics | 4.1 | 1.4 |
| Alkyl Bromides | 0.4 | 0.2 |
| Conversion | 20 | 23 |
| Yield (%) | | |
| Yield of acyclic C3-C6 olefins | 14.7 | 19.4 |
| Yield of ethylene | <0.002 | <0.023 |
| Yield of aromatics | 0.8 | 0.3 | silicalite from the MFI family
†as defined from TPD measurement

The decrease in the conversion rate from example 1 (>99%) compared to examples 2 and 3 (<25%) is explained by a higher velocity used in the reaction (WHSV >5 $h^{-1}$).

It is notable that the lowest yield in the production of C3-C6 olefins (14.7%) achieved in example 2 is still higher than the yield shown in the comparative example 1 (<10.4%) wherein HZMS-5 with a low SAR of 30 was used. Using the best conditions of the process, namely using a catalyst composition comprising silicalites, magnesium and phosphorus, a yield of 19.4% (example 3) can be achieved while minimizing the production of ethylene and aromatics.

The modification of the one or more zeolites with phosphorous, and ultimately with a combination of phosphorous and magnesium has allowed for obtaining a steady conversion with high selectivity for light products for 48 hours with a steamed catalyst.

Example 4: Stability Studies of the Catalyst

Using the catalyst composition of example 1, namely a silicalite from the MFI family with $SiO_2$ as a binder, the conversion plot of $CH_3Br$ into C3-C6 olefins over time was obtained.

The conditions reaction for this stability experiment are indicated in table 3:

TABLE 3

Conditions reaction of example 4

| SAR† | >150 |
|---|---|
| Temperature (° C.) | 280 |
| Pressure | 6 barg |
| WHSV ($h^{-1}$) | 2.0 |
| $N_2/CH_3Br$ (mol/mol) | 7/3 |
| Partial pressure of $CH_3X$ | 2.1 bara |

†as defined from TPD measurement

Figure 4:
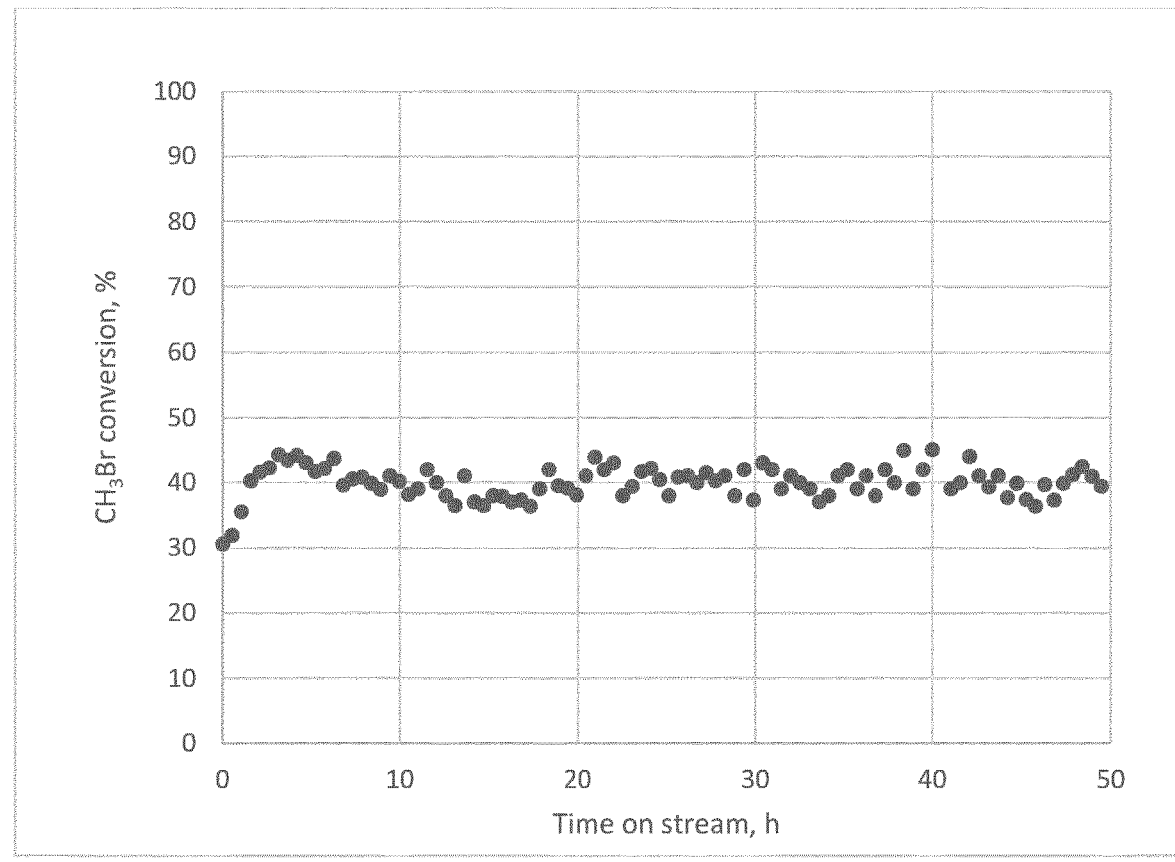
FIG. 4 shows the conversion trend of methyl bromide thanks to the catalyst according to the disclosure.

The conversion plot of methyl bromide is reported in FIG. 4 and shows, after a quick increase of the reaction rate during the first hour, a steady conversion comprised between 35% and 45% for at least 10 hours. The experiment was also conducted for a period of time of 50 hours and no decrease of the conversion has been observed, as shown in FIG. 4.

The invention claimed is:

1. Process for converting one or more alkyl halides to acyclic C3-C6 olefins said process comprising the following steps:
    a) providing a feedstream comprising one or more alkyl halides; optionally, diluted in at least one diluent;
    b) providing a catalyst composition; and
    c) contacting said feedstream with said catalyst composition under reaction conditions;
the process is characterized in that it the further comprises a step of steaming said catalyst composition before the step (c) and in that said catalyst composition comprises one or more zeolites and a binder, wherein said one or more zeolites comprise at least one 10-membered ring channel and contain less than 5000 wt. ppm of transition metals as determined by XRF based on the total weight of the one or more zeolites; and further wherein said one or more zeolites of the catalyst composition have a Si/Al molar ratio in the framework of the zeolite of at least 10 as determined by TPD before the step of steaming.

2. The process according to claim 1, characterized in that the binder is free of alumina.

3. The process according to claim 1, characterized in that said one or more zeolites of the catalyst composition have a Si/Al molar ratio in the framework of the zeolite of at least 80 as determined by TPD after the step of steaming.

4. The process according to claim 1, characterized in that said one or more zeolites of the catalyst composition are free of metal other than aluminium as extra framework.

5. The process according to claim 1, characterized in that said one or more zeolites of the catalyst composition are free of gallium and/or cerium and/or zinc.

6. The process according to claim 1, characterized in that said step of steaming is followed by an extraction step.

7. The process according to claim 1, characterized in that the one or more zeolites in the catalyst composition are one or more selected from the group of MFI, MEL, FER, MTT, MWW, TON, EUO and MRE frameworks.

8. The process according to claim 1, characterized in that said one or more zeolites are or comprise MFI zeolites.

9. The process according to claim 1, characterized in that said binder is selected from silica, clays, calcium phosphates, magnesium phosphates and mullite.

10. The process according to claim 1, characterized in that said one or more zeolites have Brønsted acid sites in a concentration less than 100 μmol/g-cat as determined by $NH_3$-Temperature Programmed Desorption.

11. The process according to claim 1, characterized in that said catalyst composition further comprises at least 0.1 wt. % of phosphorous based on the total weight of the catalyst composition.

12. The process according to claim 11, characterized in that said catalyst composition is blended with at least one metal-containing material.

13. The process according to claim 12, characterized in that the at least one metal-containing material is an alkaline earth metal-containing material which comprises at least one alkaline earth metal selected from beryllium, magnesium, calcium, strontium, barium and any mixtures thereof.

14. The process according to claim 11, characterized in that the at least one metal-containing material has an anion selected from the group of oxides, silicates, aluminates, titanates, phosphates, borates and borosilicates.

15. The process according to claim 1, characterized in that the catalyst composition further comprises phosphoric acid and magnesium nitrate.

16. The process according to claim 1, characterized in that said one or more zeolites of the catalyst composition contain less than 1000 wt. ppm of alkali metals as determined by XRF based on the total weight of the one or more zeolites before the step of steaming.

17. The process according to claim 1, characterized in that the one or more alkyl halides in the feedstream of step (a) comprise a mixture of one or more selected from monohalo-alkyl, dihalo-alkyl, trihalo-alkyl and/or tetrahalo-alkyl.

18. The process according to claim 1, characterized in that the alkyl of said one or more alkyl halides is methyl, ethyl, propyl or any mixture thereof and/or the halogen of said one or more alkyl halides is selected from fluorine, chlorine, bromine, iodine, and any mixture thereof.

19. The process according to claim 1, characterized in that step (c) of contacting the feedstream with the catalyst composition is followed by a step (d) of recovering an effluent comprising acyclic C3-C6 olefins, one or more hydrogen halides, unreacted one or more alkyl halides, alkane and higher hydrocarbons and optionally said diluent; wherein the selectivity to acyclic C3-C6 olefin is at least 25%.

20. The process according to claim 1, characterized in that one or more zeolites have a crystal size below 1250 nm, as determined by scanning electron microscopy (SEM).

* * * * *